United States Patent
Edgren et al.

(10) Patent No.: US 6,652,499 B1
(45) Date of Patent: Nov. 25, 2003

(54) ABSORBENT PRODUCT WITH LATERALLY MOVABLE PORTIONS

(75) Inventors: Kent Edgren, Mölnlycke (SE); Peter Rönnberg, Mölndal (SE); Ulrika Hagrud, Göteborg (SE)

(73) Assignee: SCA Hygiene Products, Gothenburg (SE)

( * ) Notice: Subject to any disclaimer, the term of this patent is extended or adjusted under 35 U.S.C. 154(b) by 0 days.

(21) Appl. No.: 09/744,921
(22) PCT Filed: Aug. 19, 1999
(86) PCT No.: PCT/SE99/01405
  § 371 (c)(1),
  (2), (4) Date: May 2, 2001
(87) PCT Pub. No.: WO00/13640
  PCT Pub. Date: Mar. 16, 2000

(30) Foreign Application Priority Data

Sep. 4, 1998 (SE) ............................................. 9802985

(51) Int. Cl.$^7$ ................................................ A61F 13/15
(52) U.S. Cl. ........................... 604/385.01; 604/385.24; 604/385.26; 128/885
(58) Field of Search ........................ 604/385.01, 358, 604/385.26, 385.24; 128/885

(56) References Cited

U.S. PATENT DOCUMENTS

| | | | | |
|---|---|---|---|---|
| 4,182,333 A | | 1/1980 | Schaar | |
| 4,596,244 A | * | 6/1986 | Jackson | 128/855 |
| 5,324,278 A | * | 6/1994 | Visscher et al. | 604/358 |
| 5,380,310 A | * | 1/1995 | Mitrani | 604/347 |
| 5,389,094 A | * | 2/1995 | Lavash et al. | 604/358 |
| 5,527,303 A | | 6/1996 | Milby, Jr. et al. | |
| 5,591,148 A | * | 1/1997 | McFall et al. | 604/378 |
| 5,702,381 A | * | 12/1997 | Cottenden | 604/349 |
| 5,704,930 A | * | 1/1998 | Lavash et al. | 156/160 |
| 5,733,274 A | * | 3/1998 | Osborn, III | 604/358 |
| 5,772,648 A | * | 6/1998 | OsbornI et al. | 604/358 |
| 6,126,648 A | | 10/2000 | Keck et al. | |
| 6,193,701 B1 | * | 2/2001 | Van Gompel et al. | 604/370 |
| 6,387,085 B1 | * | 5/2002 | Van Gompel et al. | 604/307 |

FOREIGN PATENT DOCUMENTS

| | | |
|---|---|---|
| SE | 9701381-7 | 4/1997 |
| TW | 87116909 | 11/2000 |
| WO | 9747266 | 12/1997 |

\* cited by examiner

*Primary Examiner*—John J. Calvert
*Assistant Examiner*—Angela J Grayson
(74) *Attorney, Agent, or Firm*—Burns, Doane, Swecker & Mathis, LLP

(57) ABSTRACT

Absorbent product such as an incontinence pad, sanitary pad, diaper, absorbent inlay or the like, having a central absorbent portion with an upper permeable surface. The absorbent product also has a fluid-impermeable backsheet. In order to provide width adaptation and to allow a basin-shape to be formed in the product, two lateral portions are provided. Each of the lateral portions extends in the longitudinal direction of the product. The inner edge of each lateral portion is attached to the central portion by means of a surplus of material and the outer edge is a free outer edge. The lateral portions can thus move in a lateral direction independently of a central portion.

29 Claims, 11 Drawing Sheets

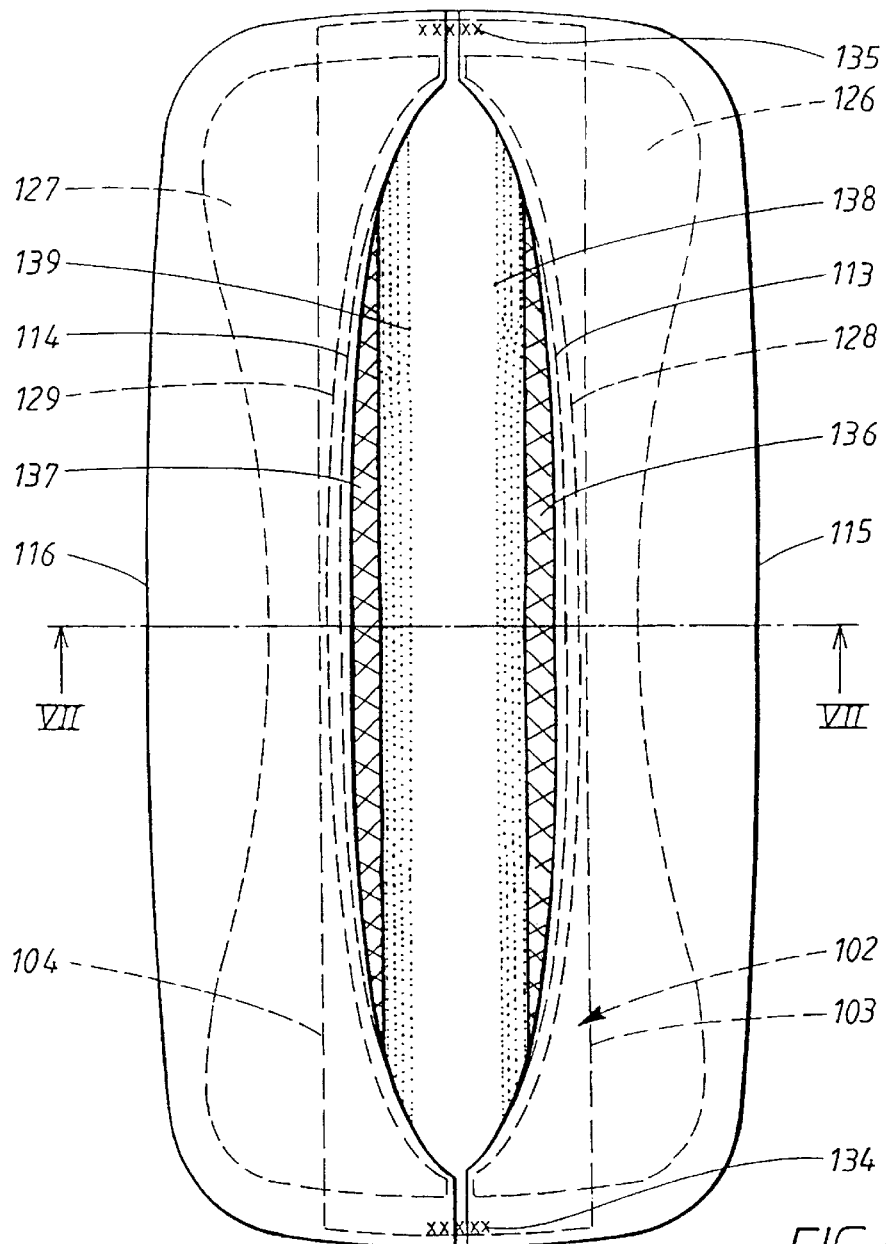
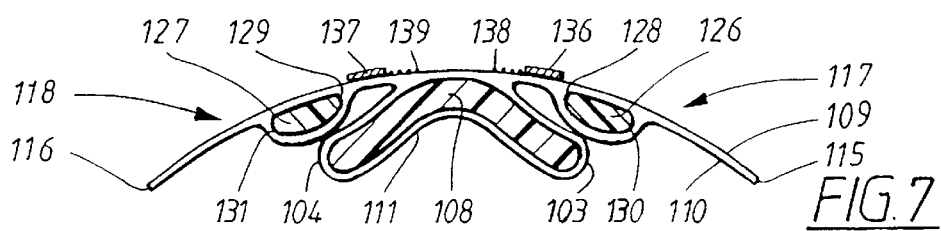
FIG. 6
FIG. 7

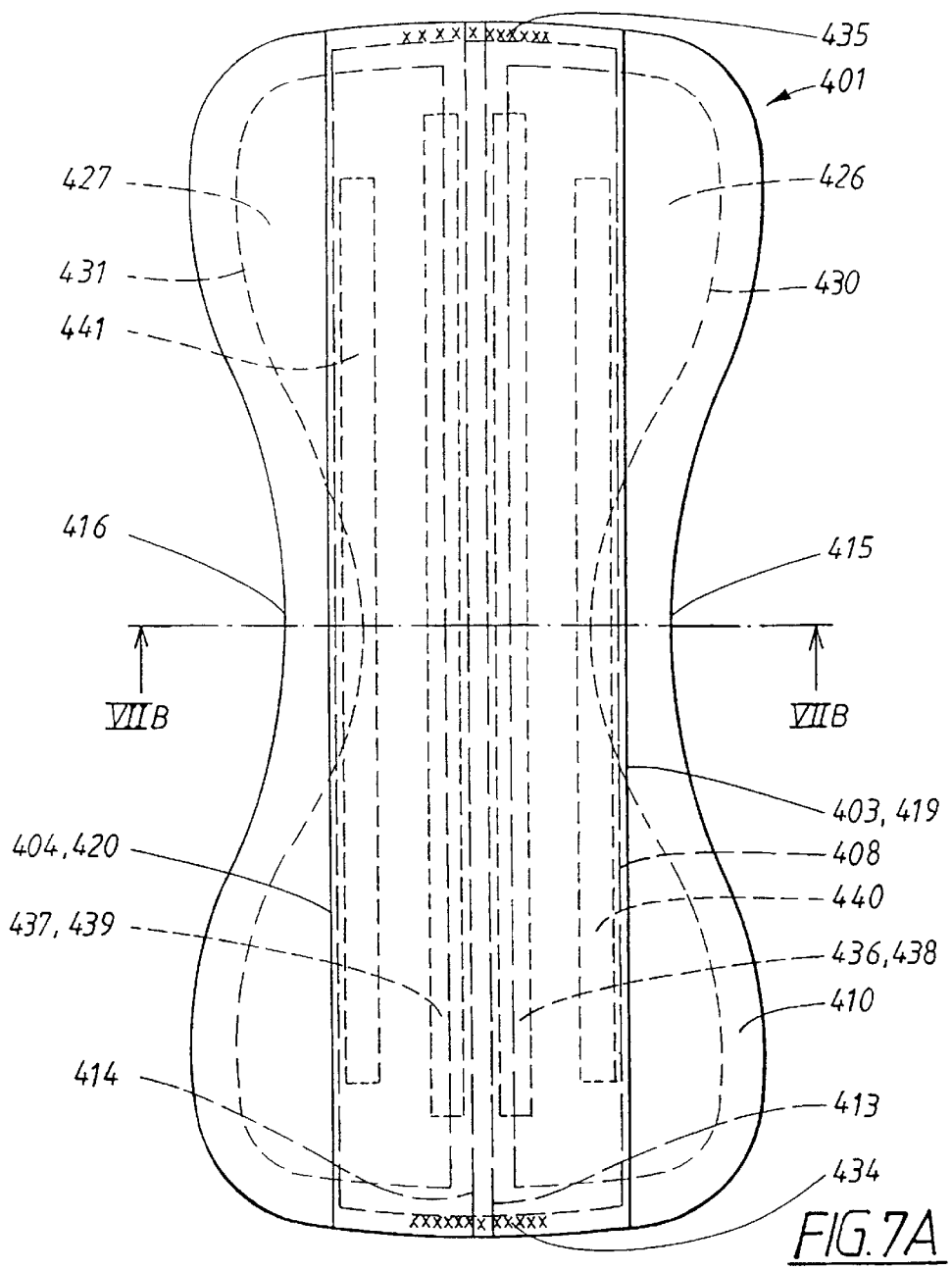
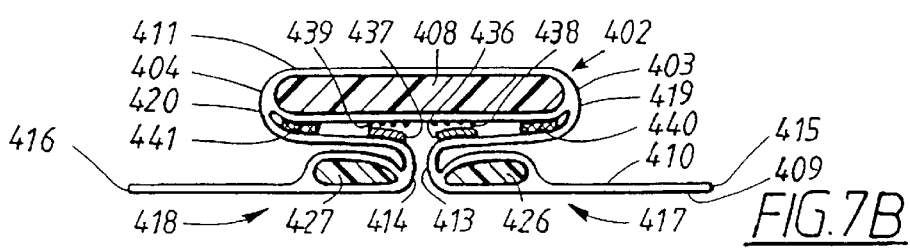
FIG. 7A
FIG. 7B (a)

(b)

(c)

ABSORBENT PRODUCT WITH LATERALLY MOVABLE PORTIONS

FIELD OF THE INVENTION

The present invention relates to an absorbent product such as an incontinence pad, a sanitary pad, a diaper, another absorbent garment, or an absorbent inlay for such a garment, or the like, for absorbing bodily exudates. In particular, but not exclusively, the invention relates to absorbent products which are disposable after use (i.e. of the type which have materials which are not intended to be washed and used several times). Still more particularly, the invention relates to incontinence products, especially for use by adults, primarily but not exclusively for adult feminine use.

BACKGROUND OF THE INVENTION

Typically, absorbent products of the above-mentioned type have an absorbent core surrounded by an envelope comprising a fluid-impermeable sheet or layer (commonly referred to as a back sheet) and a fluid-permeable sheet or layer (commonly referred to as a liner, top sheet or bodyside layer). In order to provide relatively fixed positioning of such products with respect to the wearer's undergarment, friction-increasing means, such as one or more strips of pressure sensitive adhesive or the like, are applied to the outer surface of the back sheet. The presence of the friction-increasing means helps to inhibit movement of the absorbent product with respect to the undergarment by frictional engagement therewith. Prior art products of the this type are known in the art. In order that absorbent products conform better to the shape of users, and in particular to the wearer's genitals, it is desirable to form absorbent products with a bowl or basin shape therein. Such a shape improves comfort.

Prior art solutions to said problem involve manufacturing methods including moulding articles into a basin-shape, or methods in which basin-shaped inserts are fitted into the absorbent products to hold said products in the desired shape. Further solutions are known in which parts of the sides of said products are provided with elastication to pull the product into the desired shape. However products formed in these ways typically involve manufacturing complications. Moreover such products do not naturally lie flat unless forces are applied to them to hold them flat, which can lead to packaging difficulties.

One object of the present invention is to provide a basin-shaped form in an absorbent product which provides an improvement over the prior art.

A further object of the invention is to provide an absorbent product which can be manufactured as a substantially flat article, but which can simply be transformed into a basin-shape.

In co-pending, non-published Swedish application No. 9701381-7, a solution to the above problem is proposed, whereby one or more pleats is provided in the impermeable back sheet of the product. Due to the use of an openable pleat, the inner folded edge of said pleat is superposed on to the remaining surface of the back sheet. In that patent application, the inner folded edge is movable independently of the absorbent core above, but the remainder of the back sheet (which is in contact with the absorbent core) can only be moved laterally together with the absorbent core. Consequently, the absorbent core can be subject to tension forces when said pleat is opened out.

It is also a further object of the present invention to provide an absorbent product which can hold, or in other words which can "self-lock" the absorbent product into a basin-like shape.

It is also known to provide prior art products with elastication in the areas of the product adjacent the wearer's legs. In such a way a better, or tighter, fit of the product can be achieved and prevention of leakage of bodily fluids is improved. However, in many types of absorbent product, the elastication can be problematic. For example in a feminine incontinence pad, during the wearer's movements (such as walking or sitting down), a problem may arise since the outer surface of the central part of the absorbent product is held essentially in place against the wearer's undergarment by friction and also against the wearer's genitals by friction, whilst the edge portions of the absorbent product are further held by friction against the inner regions of the thighs for example. Thus when the wearer moves, although elastication may provide a reasonable seal against leakage while still allowing for movement, the wearer may experience discomfort due to the opposing forces at the central portion and the outer portions, which tends to twist the product. Additionally, a problem may arise in that, due to the wearer's movements, openings at the side edges of the product may indeed be created or enlarged, which can lead to undesirable leakage.

The aforementioned problem is often made worse by the use of friction-increasing means, such as pressure-sensitive adhesive, on the back sheet of absorbent products for fixing the central position of the product with respect to the undergarment, since slippage between the product and the wearer's undergarment is substantially prevented. However, such friction-increasing means is generally desirable per se since there are other advantages in maintaining the central part of the product in a fixed position in the undergarment.

Another object of the invention is therefore to create a product which allows for movement of the side portions relative to the central portion, in particular when the central part of the product is fixed to said undergarment.

Since the human anatomy varies greatly, also in the crotch region where said absorbent products are worn, it is desirable to create absorbent products which can adopt different dimensions.

It is therefore another object of the invention to provide an absorbent product which has means allowing a variation in the lateral width thereof (i.e. in the width direction of the product).

It is furthermore desirable that the product is able, automatically, to adopt different lateral widths during use, so as to take account of any variations in, for example, the distance between the wearer's thighs as a result of bodily movements (e.g. walking). Where such adaptation is provided, the absorbent product is more easily able to prevent leakage of bodily fluids.

It is therefore another object of the invention to provide an absorbent product which can adapt its width automatically to the width dimensions of the wearer.

A further problem which presents itself in absorbent products is that the bodily fluid to be absorbed by the product is absorbed at only the upper absorbent surface of the product. Thus, where the flow volume is large and quick, such as with flash incontinence, the absorption characteristics of the absorbent material at the bodyside surface of the product may be such that the absorbent material cannot absorb the fluid fast enough. If such is the case, the fluid can overflow laterally over the edges of the absorbent core. This increases the danger of leakage if the overflow fluid cannot be contained within the side regions of the product to allow sufficient time for absorption. Although the core can be made wider to help alleviate this problem, a wider core implies extra material costs and weight.

It is therefore another object of the invention to provide an absorbent product which has improved absorption characteristics and, in particular, a better rate of absorption.

An additional problem which presents itself in articles which have a friction-increasing means, such as pressure sensitive adhesives provided on the back sheet, is that these means need to be protected from becoming dirty or from sticking undesirably to other objects or clothing before use. To provide said protection it is known to use so-called "release paper" to cover said adhesive. When it is desired to use the product, the release paper (generally in the form of a strip) is peeled away from the underlying adhesive and discarded, thus leaving the adhesive exposed for frictional engagement with the undergarment. In order to facilitate peeling the release paper away from the adhesive, the paper is often treated with a release agent such as silicon.

Several problems arise with the use of such release paper strips. Firstly, the release paper is an element of the product which has to be discarded, which creates a litter problem. Also, the release paper has no further use in the absorption function of the product and thus the provision of such release paper is clearly wasteful and adds to production costs. Furthermore, in use, it has often been found difficult to grasp a non-attached edge of the release paper in order to peel it away from the rest of the product.

A solution to these problems has also been provided by the aforementioned co-pending Swedish application.

One further object of the present invention is however also to provide a product which obviates the use of release paper whilst still providing an effective barrier against direct external contact with an area of the product on which the friction-increasing means may be placed.

Further problems which can be solved by this invention with respect to known absorbent products will become apparent below.

SUMMARY OF THE INVENTION

The present invention provides a solution to the aforementioned objects. A solution to at least some of the objects is provided by an absorbent product having the features defined in claim 1.

Preferred features of the invention are defined in the dependent claims.

It should be understood that the term "friction-increasing means" as used herein, is intended to imply either a surface texture, or a formation on, or coating of, or treatment of, a sheet or layer which has the effect of increasing the resistance of the sheet (and thus the absorbent product) to movement with respect to a user's undergarment, or alternatively with respect to a liner chassis, when in contact therewith. A pressure-sensitive adhesive is a suitable example of such a friction-increasing means, although different types of adhesive or other sheet treatments will be apparent to a skilled man.

Where particular dimensions are specified in the following description, it will be clear to the skilled man that the widths and lengths of the various components may also be varied in order to suit the particular circumstances. For example, the width and length of the friction-increasing means may vary widely, although typically the width of bands of adhesive may vary between about 4 mm up to several centimeters.

BRIEF DESCRIPTION OF THE DRAWINGS

The invention will now be explained in more detail with reference to certain non-limiting embodiments thereof and with the aid of the accompanying drawings, in which:

FIG. 6 shows the product of FIG. 4 with the back sheet uppermost, and in a state in which a central double pleat has been opened out on both sides to thereby form the product into its basin shape and to thereby reveal friction increasing means and a release coating therefor, FIG. 7 hows a cross-sectional view taken along line VII—VII in FIG. 6, FIG. 7A shows a plan view of another embodiment very similar to that shown in FIG. 4, with a structure that is easier to manufacture, FIG. 7B shows a cross-sectional view taken along line VIIB—VIIB in FIG. 7A.

In the figures, the cross-sectional views are not drawn to scale for reasons of clarity and thus many parts thereof would appear far thinner and also closer together in practice. Similarly, the cross-sectional views of the permeable and impermeable material sheets have been drawn as single solid lines and not as hatched lines, since otherwise a false understanding of the lay-up of the layers might occur.

DETAILED DESCRIPTION OF THE PREFERRED EMBODIMENTS

Figure 1:
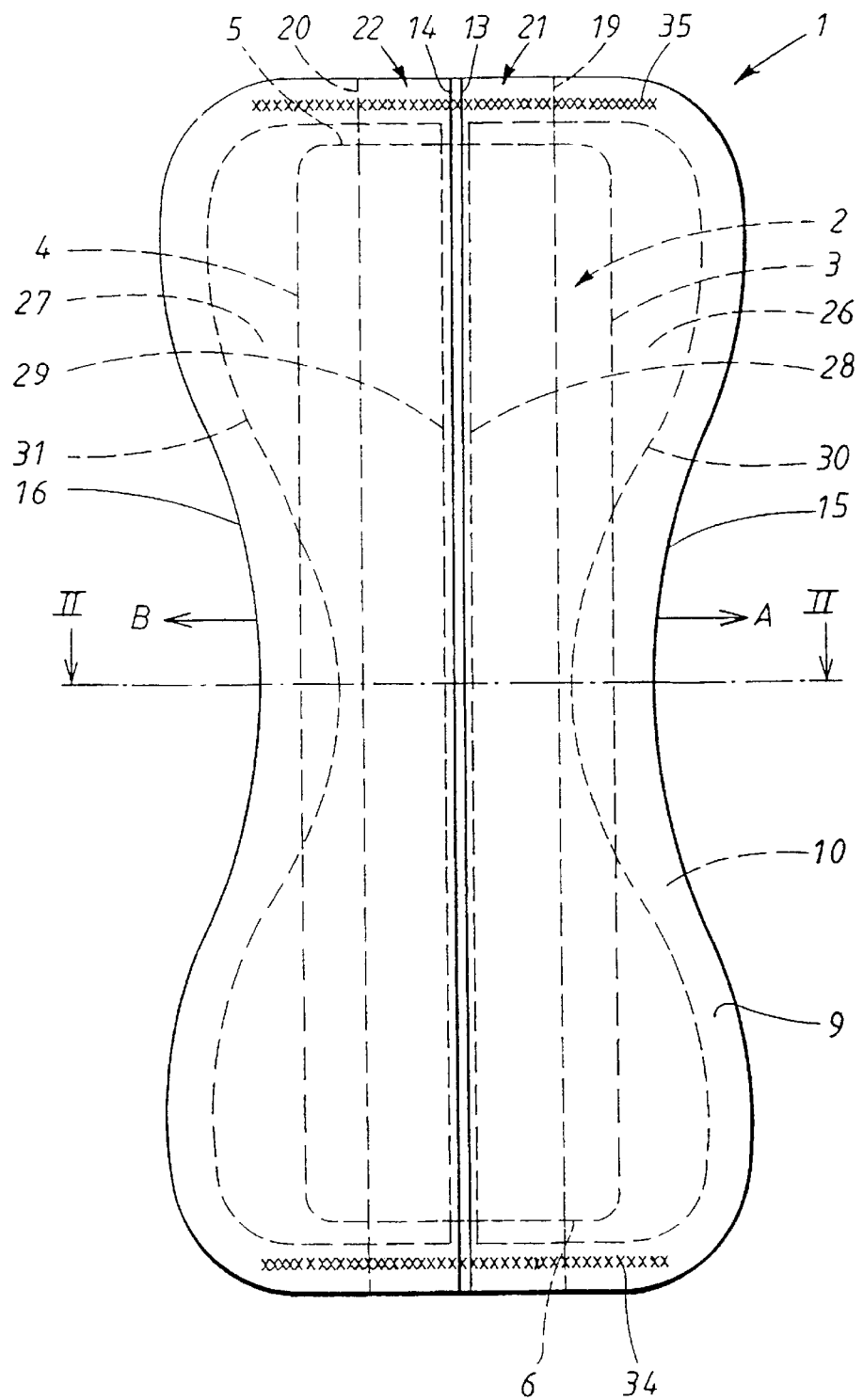
FIG. 1 is a plan view of an incontinence pad embodying the present invention, with the backsheet-side of the product shown uppermost.

The absorbent product 1 in FIG. 1 is a feminine incontinence pad, or sanitary pad, embodying the present invention. In the plan view shown, the product is in the flat condition with its impermeable back sheet 9 uppermost. The longitudinal direction of the product runs from the top to the bottom of the page while the lateral direction runs across the width of the product, generally perpendicular to the longitudinal direction.

The product has a central absorbent portion 2 shown in dashed lines. The central portion 2 has two straight and generally parallel outer longitudinal edges 3, 4 and two curved end edges 5, 6. However, said central portion may have other shapes with curved longitudinal edges. Said central absorbent portion comprises absorbent material 8 (see FIG. 2), such as cellulose pulp, surrounded on all sides by a single liquid/fluid-permeable layer 7. The material of layer 7 can be any suitable permeable material, but particularly those which are comfortable against the skin such as non-woven materials. Non-woven materials of the spunbond type are suitable, such as for example a PP spunbond having a surface weight of 22 $gm^{-2}$.

The central absorbent portion 2 is positioned generally midway between the outer edges of the product 1. The central absorbent portion has an upper body-facing surface 11 and an opposite lower surface 12.

A single back sheet 9, made of liquid/fluid-impermeable and substantially non-elastic material, is shown uppermost in FIG. 1. Materials for such sheets are well known in the art and do not require detailed description. The backsheet 3 should however preferably also have good resistance to tearing and a material such as a polyethylene sheet as used in current absorbent products would therefore be suitable.

Attached to one side of back sheet 9, at least at the outer periphery thereof, is a fluid-permeable sheet or layer 10. The longitudinal outer peripheral edges of the absorbent product 1 are denoted 15 and 16 respectively. As will be explained below, said edges also form the respective outer edges 15 and 16 of two lateral portions 17 and 18.

Figure 2:
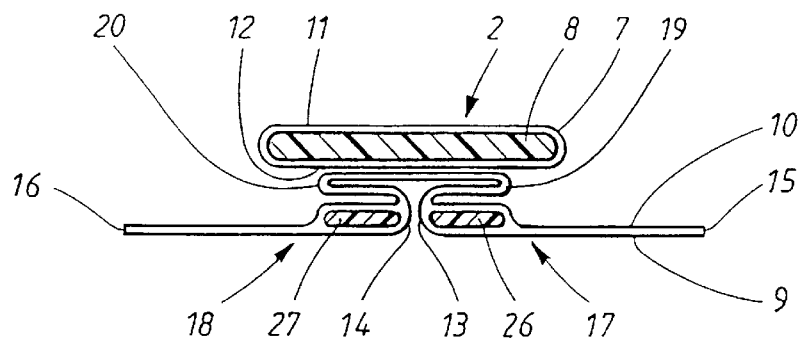
FIG. 2 is a cross-sectional view taken on line II—II in FIG. 1, however with the back sheet shown lowermost.

Two pleats 21 and 22 of a double pleat are formed in the product, said pleats having inner edges 13 and 14, with a curved apex, running longitudinally and generally parallel to the central longitudinal axis of the product. Said inner edges 13 and 14 may also be touching, or overlapping if desired. As can be seen in FIG. 2, each of said pleats 21 and 22 is formed by pleating (i.e. S- or Z-folding at least once) the back sheet 9 and, in this case, also sheet 10. In the preferred form as shown, the opposite curved apex of each edge 19, 20 of the pleats has been arranged to lie well inside the outer edges 3 and 4 of the absorbent core, for reasons to be explained below.

Figure 2A:
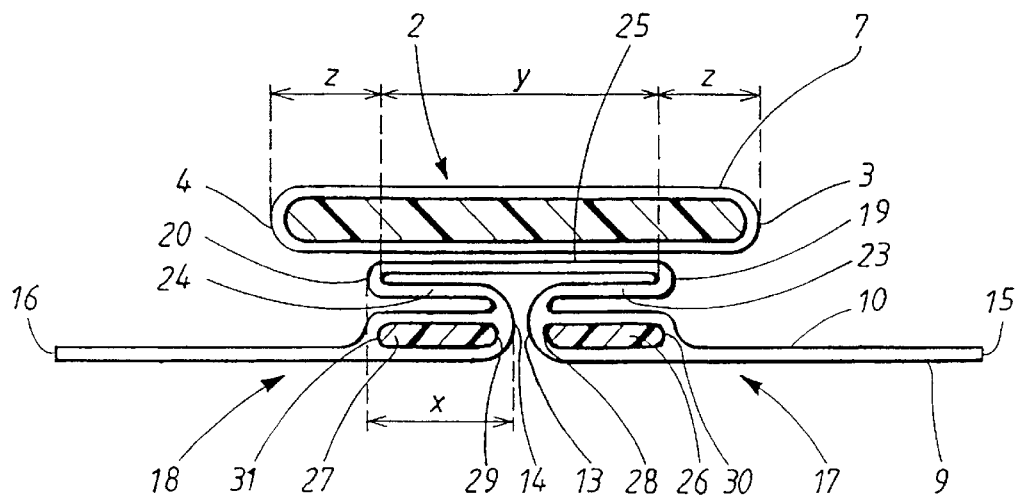
FIG. 2A shows an enlarged view of the cross-section of FIG. 2.

As can be seen in FIG. 2A, the distance between the apex 14 and the apex 20 of the left pleat's edges defines a surplus of material 24 of approximate length "x". Similarly, a surplus of material 23 will be provided on the opposite side. Normally the material surplus on each side will be substantially equal in length.

Two lateral portions, generally denoted 17 and 18 are provided below the central absorbent portion 2 and to the sides of its longitudinal axis. The lateral portions 17 and 18 have outer longitudinal edges 15 and 16, and inner longitudinal edges 13 and 14 respectively.

The planar upper portion 25 of the double pleat is attached to the central absorbent part 2 by means of adhesive or the like (not shown) on the upper outer surface of sheet 10 within zone "y". Said attachment may be permanent or releasable. Similarly, it is preferable if sheets 9 and 10 are connected in the regions of the surplus material 24 and 23 as well as between outer edges 15 and 16 and each edge 13 and 14. In particular, the sheets 9 and 10 should normally be connected to each other at each respective edges.

Between sheets 9 and 10 there are two stiffening members 26 and 27, which are to stiffen the region of the pleat close to the inner edges 13 and 14 of each lateral portion 17 and 18. Said stiffening members should allow at least a small degree of bending for a purpose to be explained below. Whilst said stiffening members/portions 26, 27 may merely be simple strips of stiffening material such as non-woven material strips or the like, it is preferred that said stiffening members are formed by thin strips of absorbent material such as cellulose fluff material. A stiffening strip thickness of about 1 mm and width of about 10 mm has been shown to be entirely satisfactory, although it should be understood that a stiffening strip is not essential but merely preferable.

As can be seen in FIG. 1 the absorbent portions 26, 27 are formed as two substantially half hourglass shapes having a straight longitudinal inner edge 28, 29 and a curved outer edge 30, 31 respectively. This shape is not a requirement, but is preferable as will be explained below.

In use, in certain embodiments,, it is intended that most of the bodily fluid to be absorbed should be absorbed by the central absorption portion which will have initial, or primary, contact with the main volume of bodily fluid to be absorbed. In this case, it is preferred if the portions 26 and 27 are of less thickness than the central portion 8.

Preferably, the portions 26 and 27 can suitably be less than about 50% of the thickness of the central absorbent portion and more preferably between about 5% and 20% of the thickness of the central absorbent portion. Since the absorbent material pieces 8, 26 and 27 are all separate, there is no difficulty during production in providing such different thicknesses in the different regions of the product.

In the aspect of the invention in which a basin-shaped product is to be formed from the flat product in FIG. 1, each of the pleats 21 and 22 is sealed together at areas 34 and 35, at least at the end portions of the inner edges 13 and 14 and edges 19 and 20.

In order to vary the actual form of the basin shape (i.e. to vary where the maximum curvature is present in the longitudinal direction of the product), the position of pleat sealing can be varied. For example, in male incontinence products the maximum curvature should clearly be closer to one end of the product and thus the openable part of the pleat(s) would be arranged closer to that one end.

The portion 25 of the double pleat is attached to the outer permeable layer 7 of central portion 2 over a distance "y". Since the portion 2 is longer than "y", this leaves two non-attached portions of length "z" on the lower surface of portion 2, extending approximately between the pleat apex 19, 20 respectively and the outer longitudinal edges 3, 4 respectively of the portion 2.

Figure 3:
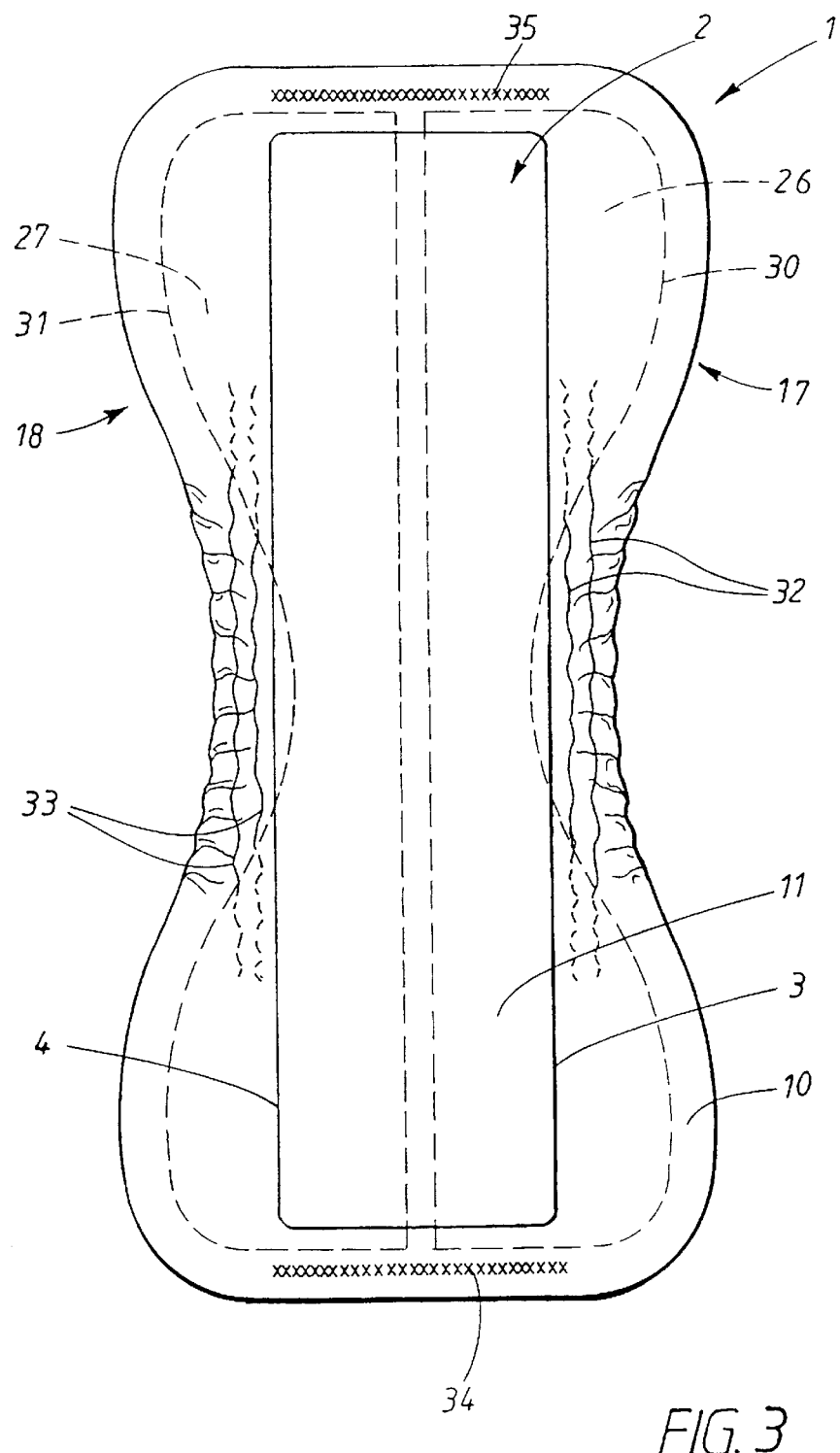
FIG. 3 is a plan view of the product shown in FIG. 1, shown with the central absorbent core uppermost, and in which Figure elastication has been added at the outer edges of the lateral portions.

In FIG. 3 certain detail lines have been omitted for reasons of clarity, thus leaving visible only the central absorbent portion 2 and the two lateral portions 17, 18 with respective absorbent portions 26, 27. Additionally, in this preferred embodiment, elastic threads 32, 33 (preferably in pairs) have been affixed to both the permeable sheet 10 and the back sheet 9. The threads 32, 33 extend longitudinally over the longitudinally central part of the lateral portions 17 and 18, at the outer edges thereof.

It should also be noted that in the condition as shown, the absorbent product is flat and the elastic forces provided by threads 32 and 33, do not cause said product to try to assume a basin-shape and thus said product remains substantially flat without requiring the application of external forces to remain flat. Instead, said elastic threads serve to shorten, or in some cases merely maintain (when affixed to the product in a non-tensioned state), the natural length of the outer edge parts 15 and 16 of the lateral portions 17 and 18.

As will be clear from the aforegoing description and figures, both the inner edges 13, 14 and the outer edges 15, 16 of the lateral portions 17 and 18 can move laterally inwardly and outwardly independently with respect to the central absorbent portion 2 by unfurling the portions 23 and 24 of the pleat. Thus, as will be appreciated, if the product was fitted to the inside of an undergarment, the central portion 2 could be affixed to the undergarment, whilst the two outer portions 17 and 18 can be adapted to the shape of, and adapted to follow the movement of, the inside of the wearer's thighs for example. In this way, the width of the product can vary automatically, since lateral inward and outward movement of the lateral portions 17 and 18 each by a maximum amount of distance "x" in the crotch region is possible. Similarly, due to the surplus of material in each section 23, 24, some independent longitudinal movement of the side portions 17, 18 with respect to the central portion 2 will also be possible. Where the ends of the pleats are however fixed together as at 34 and 35, longitudinal movement as described in the preceding paragraph will no longer be possible. However in such a case, automatic width adaptation is still provided.

Moreover, the aspect of forming a bowl-shaped product is fulfilled when the ends are joined at 34 and 35 and the lateral portions pulled out in a direction as shown by lateral outward forces on the lateral portions 17 and 18 applied in correspondence with arrows A and B in FIG. 1 for example. Said forces will cause the pleats 21, 22 to open out fully in the central region and by a gradually lesser degree along their length up to the areas 34 and 35, whilst the central absorbent portion 2 has no lateral forces applied thereto by said pleat-opening movements. Since the inner edges 13 and 14 of the pleats however are required to assume a greater length when forces are applied at A and B, the lateral portions 17, 18 attached to the edges 13, 14 will be caused to assume a hollow, arcuate half-bowl or half-basin shape on either side of the longitudinal centreline. In this way, as the outer edges 15 and 16 are moved further apart, the product takes on a whole hollow basin shape with curvature both in the lateral as well as in the longitudinal directions. Opening of the pleats in this way and the subsequent formation of a basin shape, will also become more easily apparent from FIG. 6 and FIG. 7 to be explained below.

Thus, by this simple arrangement and simple outward force application, the flat product can be transformed into a basin-shaped product.

When elastication 32, 33 is used in the outer edge parts of the lateral portions 17, 18, the elastic will stretch slightly during outward lateral movement. Thus the elastic will provide a certain holding force causing the basin-shaped product to try and maintain the basin shape. However, lateral forces which may be applied by the wearer on the side portions of the article will cause the lateral portions to move inwardly slightly and thus decrease the width of the product. Thus, an automatically variable and width-adapting product is obtained which will have a resilient force therein attempting to maintain its shape.

Furthermore, since the movements of all three portions 2, 17, 18, in the lateral direction of the product is independent, the article can separately adapt to movements which might only require a width change, or lateral movement, on one side of the product.

From the above it will be clear that where friction-increasing means (depicted in later embodiments) is applied to the central portion 2 for frictional contact with a wearer's undergarment, this part can remain stable and fixed to the user's undergarment, while the two lateral portions 17 and 18 can move laterally independently of the central portion 2. In this way, better leakage sealing is provided while still maintaining the product in place and in a basin-shape.

As is shown in FIG. 2A, the two portions of length "z" overlying the top part 25 of the pleats 21 and 22, has a lower surface, upper surface and curved end portions through which fluids may be absorbed. Thus, an extra fluid absorption surface for the same absorbent material 8 is provided on the lower surface thereof. When the lateral portions 17, 18 are moved laterally outwardly to unfurl the pleat portions 23 and 24, the absorbent part 2 will be brought closer to back sheet 9. The cross-section will also have assumed an arched shape. When the product is in use, fluids will normally enter the absorbent material 8 from above. However, when the rate of fluid release is too high, fluid may overflow over the lateral edges of the absorbent portion 2 and on to the sheets 9 and 10. Any fluid entering this region between edges 3 and 4 and the sheets 9, 10 will then be able to flow to the underside of the central portion 2 up to where the area 25 is attached and be absorbed over that surface. Thus, compared to an absorbent product allowing absorption only from above, the rate of absorption will be better in the invention if the same core materials are used. This allows for example thinner cores to be used if desired.

Since overflow over the central portion 2 will not always occur, the absorbent portions 26 and 27 can also be kept very thin, of the order of 1 to 4 mm thickness for example (as measured optically in the uncompressed state).

In embodiments where the ends are sealed as at 34, 35 and the lateral portions 17, 18 are moved outwardly, the maximum pleat opening will be in the central region of the product. Thus, the longitudinally-central parts of the absorbent materials 26 and 27 will move a maximum distance laterally outwardly and the end regions will move outwardly to a lesser degree. Thus, to provide absorbent material 26 and 27 which is both underneath and laterally outwardly beyond the longitudinal edges 3 and 4 all the way along the central portion 2, a half hour-glass shape is suitable for each absorbent section 26, 27. A similar construction in this regard is also visible in FIGS. 6 and 7.

Although the surplus material is provided in the form of a vertically arranged pleat, it is possible to arrange the surplus of material, in some cases, as a horizontally pleated portion (i.e. with a lateral pleated gathering of the material).

Figure 4:
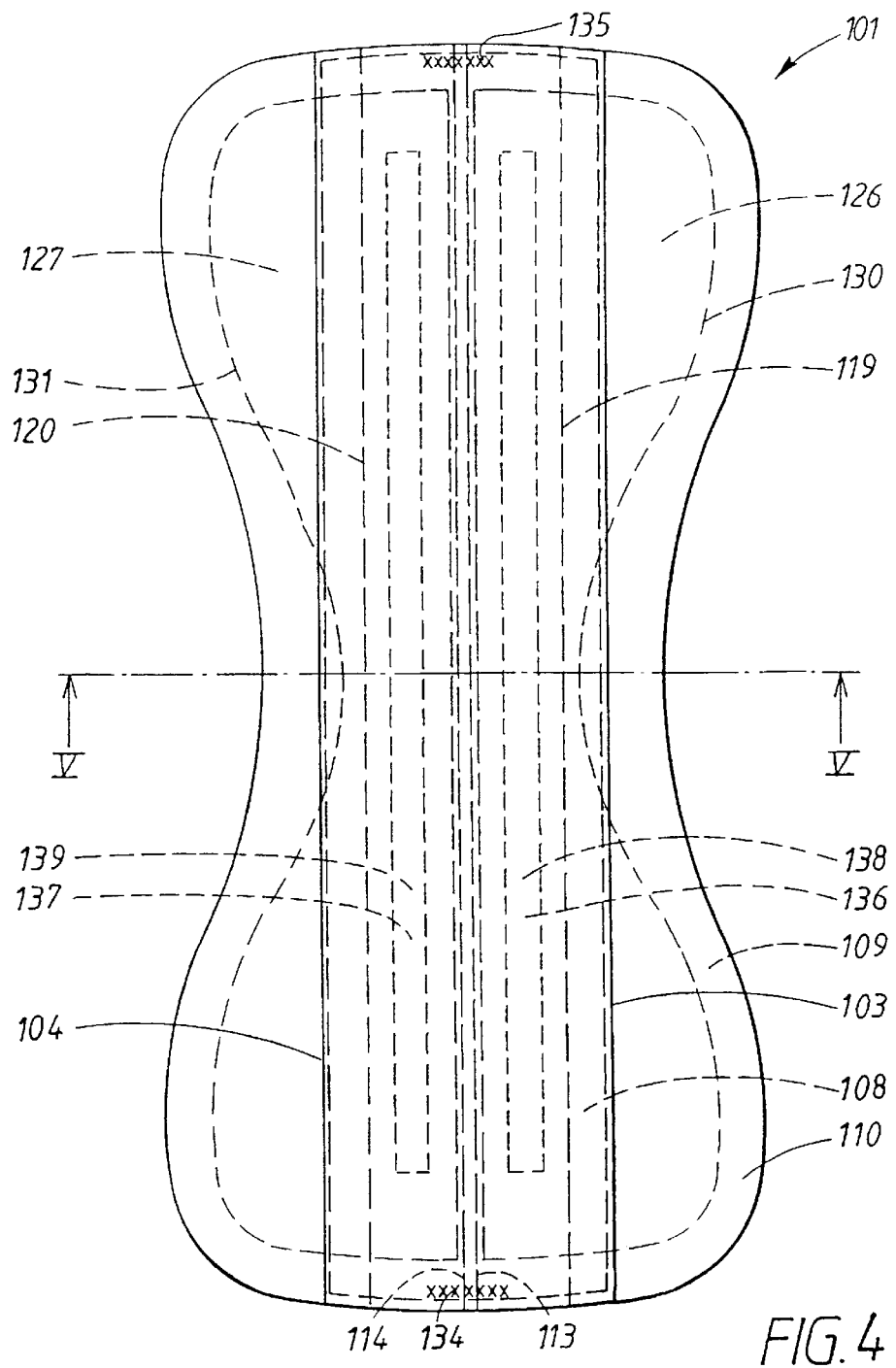
FIG. 4 shows a second embodiment of the product of the invention, in which only one top sheet is used and viewed with the central absorption portion uppermost.
Figure 5:
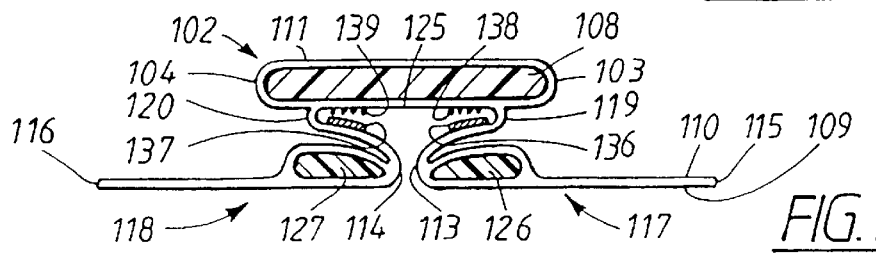
FIG. 5 shows a cross section through line V—V in FIG. 4.

A second embodiment of the invention is shown in FIGS. 4 to 7. FIGS. 4 and 5 depict the flat state of the product whilst FIGS. 6 and 7 show the opened-out state of the product. The same reference numerals, raised by 100 compared to the first embodiment, have been used in the second embodiment to denote similar features. No elastic threads are shown in this embodiment corresponding to threads 32, 33 of the first embodiment. However such elastication may be included where desired, in a similar manner to the first embodiment.

FIG. 4 shows an absorbent product 101 viewed from above on to the body-facing side of the absorbent portion 102. The construction is very similar to the first embodiment and therefore need not be described in the same detail.

However it should be noted that the back sheet 109 formation and the top sheet formation 110 are different to the previous embodiment. Friction increasing means 136, 137, shown in the form of an applied layer in each pleat has been included on an upwardly facing surface of the surplus material portion of said pleat. On an opposing surface in said pleat, there are release means 138 and 139 respectively, here depicted as a line of small dots. The release means may be formed by a silicon coating or other coating, or by making sheet 109 as a plastified silicon sheet, or in another way. The release means typically has a small affinity for the material 9 such that it can be pealed away therefrom without large forces being applied. In a less preferred embodiment of the invention (not shown) release paper may be applied to the friction-increasing means to thereby cover it.

It is to be noted that said release means and friction increasing means can be included in all embodiments of the invention. Similarly, the surface(s) on which said release means are present and said friction-increasing means are present may vary. Friction increasing means can if desirable only be included in one pleat, or only on the central portion 125 of the pleat. The pleats should however cover most of, and normally all of, the friction-increasing means to avoid it being able to contact other surfaces before the pleats are opened out (see the opened out state in FIGS. 6 and 7).

In this second embodiment, only one back sheet 109 and one top sheet 110 have been used. Both of said sheets are pleated, although the formation of the pleats is slightly different than the first embodiment in as far as the upper ends are concerned. Instead of sheet 110 following sheet 109 right through the attachment area (as in the first embodiment), the permeable sheet instead 110 goes around the absorbent core material 108 and forms the body-facing surface 111 of portion 102. However, it should be noted that the sheets 109 and 110 should preferably be fixed to each other up to the location, at apex 119 and 120 where the sheets 109 and 110 take different paths. The sheets 109 and 110 are even preferably attached all the way from edges 115, 116 to apex 119, 120 respectively (with the exception of the area around the absorbent portions 126 and 127 if these are included in the product, which is optional).

As is clear from the figures, the friction-increasing means 136, 137 are concealed entirely between one fold of the pleat, when the article is in the flat condition, such that they cannot contact other surfaces (e.g. clothing) before the pleats are opened out.

Whilst the friction-increasing means is generally applied as a continuous strip of material along the product (as indicated by FIGS. 4 and 6 for example), the strip may be a series of intermittent areas or zones of friction-increasing material. Furthermore one or more of said zones may comprise distinct areas of friction-increasing material such as dotted areas arranged in particular patterns. This is particularly suitable in the context of adhesives, but is also applicable to other types of friction-increasing means. In this way it may be possible to reduce the cost of the friction-increasing material. For example, the two continuous strips 136, 137 shown in FIG. 4 might each be divided into two or more spaced thinner strips, preferably running substantially parallel to one another.

When it is desired to use the absorbent product, the pleats can be opened up, or unfurled, as already explained with reference to the first embodiment. The opened-up situation is shown in FIGS. 6 and 7.

However, it should be noted that not all users always wish to have "basin-shaped" products and thus the products can be used in an unopened condition, if desired. This applies to all embodiments.

However, in the normal case where it is desired to make use of the friction-increasing means 136, 137 by exposing it for contact with an undergarment or the like, the user may grip the outer longitudinal edges of the flat product and exert a lateral force on the backsheet in the direction of opposed arrows A and B as described previously. By doing this, the product will open out into a basin shape as shown in FIGS. 6 and 7. Due to the construction of the product (i.e. with the central portion being attached only by surplus material to the two lateral portions) such opening movements will not apply undesirable tension forces to the central absorbent part.

In FIG. 6, the pleat has been opened out between the areas of sealing 134 and 135, from a minimum of opening out at either longitudinal end, to a maximum of opening-out at the central area between the two seals 134 and 135. Since the edges 113 and 114 are still visible as pleated edges in about the first quarter length of the product from each end, these edges have been drawn as solid lines in that region, whilst they transform into dashed lines in the central half of the product, since the edges 113 and 114 are opened out in that region although the crease lines in the product will still be visible. Thus, the edges 113 and 114 run in a curvilinear fashion from one seal 134 to the other 135.

As can also be seen, the product 102 has assumed a basin-shape and substantial areas of the friction increasing means 136, 137 are uncovered, for later contact with an undergarment. Similarly, the strips of applied release means 138 and 139 are visible adjacent the friction increasing means.

From FIGS. 6 and 7, it can be clearly seen how the inner edges 128, 129 of the lateral absorbent portions 126, 127 lie underneath (in the normal use orientation) and laterally inside the outer edges 103, 104 of the central absorbent portion 102. A certain amount of friction, helping to self-lock the product in this bowl-shaped orientation, occurs between the touching sheet portions located between the adjacent absorbent material section 108, 126 and 108, 127 respectively. It should however be remembered that this self-lock function can also be enhanced by elastic threads or the like being applied to the central longitudinal portions of the lateral portions 117, 118 as in the first embodiment as well as the natural self lock-effect of the lateral portions in an opened-out position.

Figure 14:
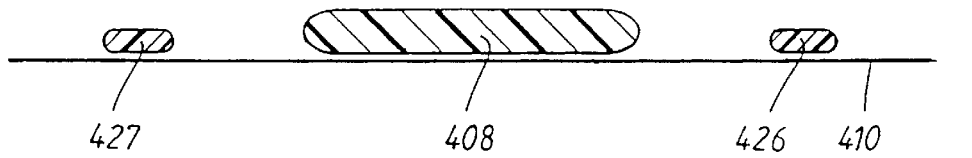
FIG. 14 shows three steps, denoted as steps (a) to (c), in the manufacturing process of the product in FIGS. 7A and 7B.
Figure 14:
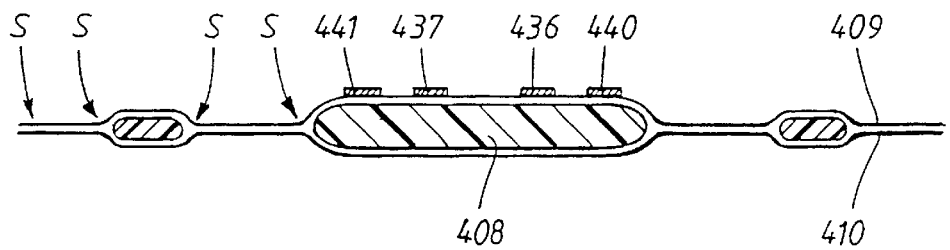
Figure 14:
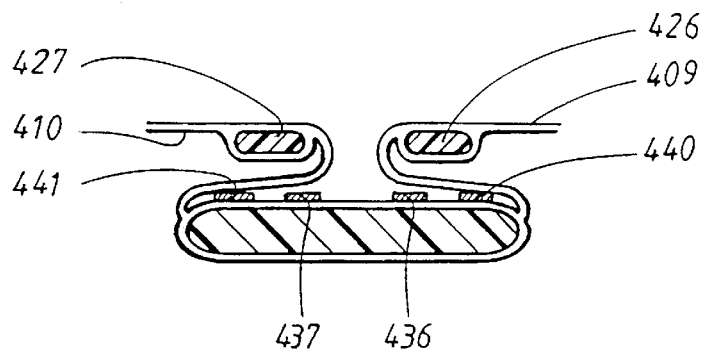

FIGS. 7A and 7B show a variation of the embodiment shown in FIGS. 4 to 7. This variation concerns an article which can be manufactured more simply than the aforegoing one. This comprises two sheets (a top sheet layer 410 and a back sheet layer 409) with an absorbent core 408 and two preferably absorbent parts 426, 427 placed between said sheets. The sheets are intended to be the same unstretched length (i.e. running from left to right in the figures, as also shown in FIG. 14). It should be understood that this structure can also be applied to any other embodiments where the absorbent and/or stiffening portions are positioned between a top sheet layer and a back sheet layer.

The top sheet and back sheet layers 410, 409 each preferably consist of one single sheet only, but each may include more than one sheet or a laminated structure. Such principles also apply to other embodiments of this invention.

For simplification, like parts have been given the same reference numerals but the numerals are raised by 400.

The structure of the article is such that the pleats on either side of the centreline are extended such that the outer apexes 419 and 420 are basically positioned at the edges 403, 404, due to the fact that the central absorbent core. This arrangement leaves an area of the back sheet 409 underlying the absorbent core right up to the longitudinal edges of the absorbent core. Adhesive 440, 441 or other connection means is used to adhere two opposing faces of the back sheet 409 in each part of the pleat. In this way, the pleat part on either side of the centreline is prevented from opening beyond the adhered locations 440, 441.

Thus, the two side parts 417, 418 may be drawn apart from each other away from the longitudinal centreline of the article (as already explained with regard to the previous embodiments), until the adhesive 440, 441 prevents further movement. Since the ends of the article are sealed at seal locations 434, 435, the bowl-shaped configuration will be obtained as explained previously.

The actual distance of the adhesive 440, 441, from either the inner or outer apex 419, 420, 413, 414 is not critical, but the skilled man will understand that its placement can determine the degree of curvature of the bowl-shape that is desired. Similarly, the adhesive 440, 441, or other seal at these locations may pass through to the top sheet in the pleat portions.

Additionally it will be noted, at variance with the previous embodiment, that the longitudinal areas of pressure-sensitive adhesive 436, 437 are placed just outside the pleat inner apexes 413, 414, facing the back sheet 410 where it underlies the absorbent core 408. Release means 438, 439, if required or desired, can be placed on said back sheet 410 overlying said areas 436, 437.

The method of manufacturing the article of the embodiment of FIGS. 7A and 7B, will be explained with the aid of FIG. 14.

Figure 10:
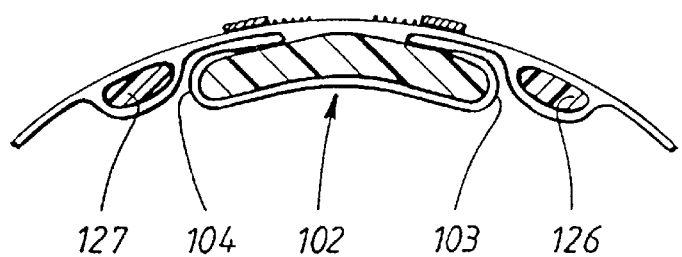
FIG. 10 shows a cross-sectional view of a product similar to that in FIG. 7, but wherein the distance between the absorbent material in each of the lateral portions is arranged to lie in adjacent contact respective outer edges of the central absorbent part.

FIG. 10 shows a further embodiment, very similar to FIG. 7, where the length of the surplus material portion of the pleat and the position of the outer edges of the portions 126 and 127 with respect to the edges 103 and 104, such that these edges lie adjacent to each other. In a further embodiment (not shown), the portions 126 and 127 may even have their inner edges overlying the edges 103, 104 of the central absorbent portion 102. As will be evident, an increased self-locking effect will thereby be present, in either of these embodiments.

Figure 8:
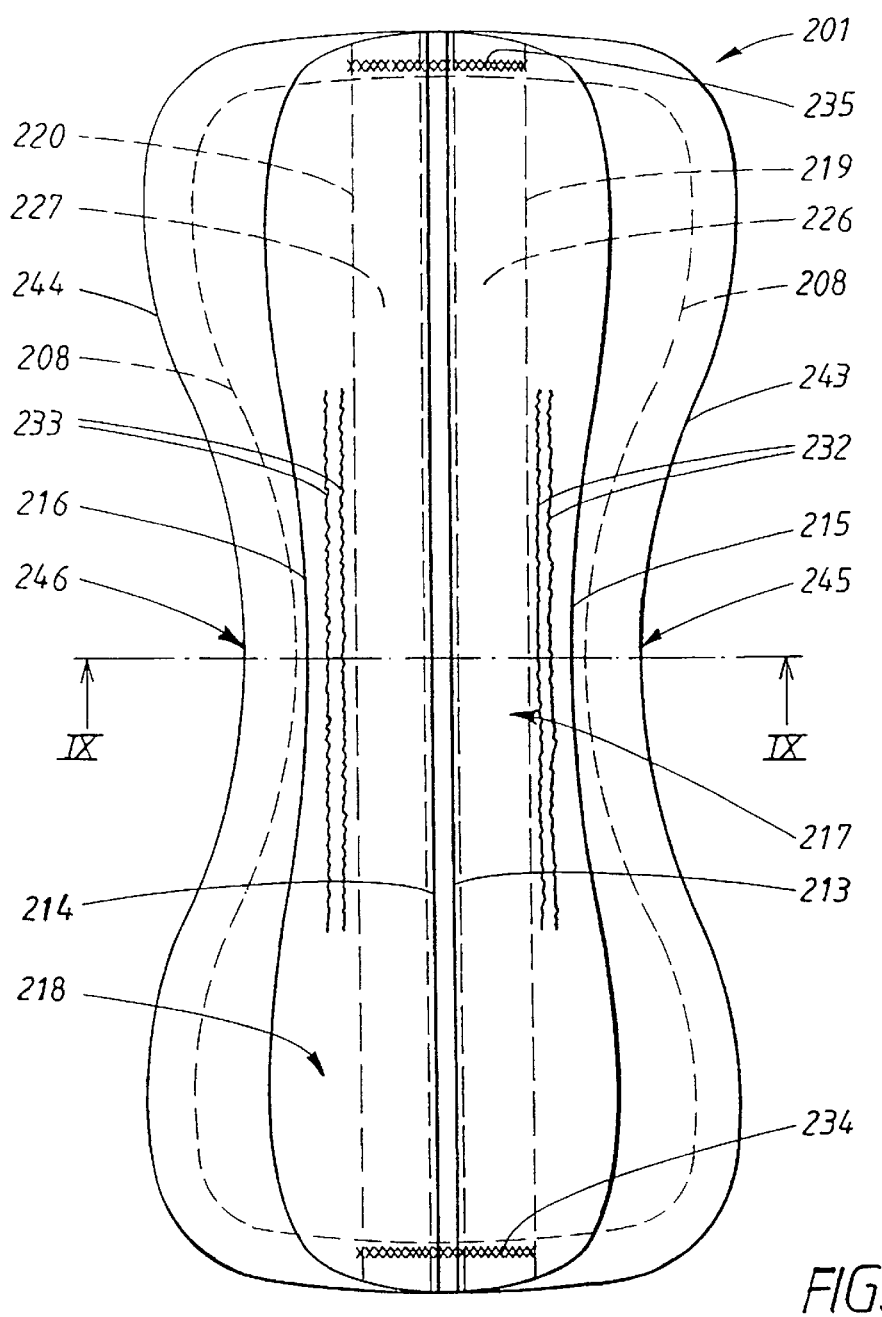
FIG. 8 shows a further embodiment of the invention, with the garment contact side of the product shown uppermost, wherein the central absorbent portion is enveloped by a top sheet and a back sheet and the two lateral portions are also enveloped by a different top sheet and back sheet.
Figure 9:
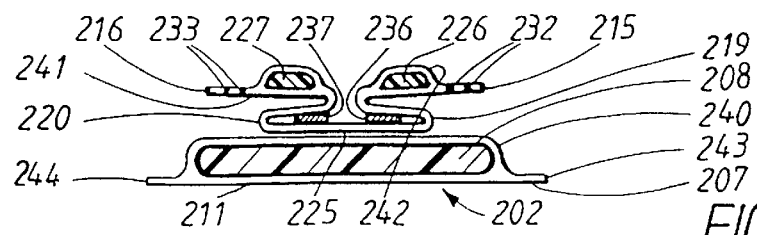
FIG. 9 shows a cross-sectional view similar along line IX—IX in FIG. 8.

In FIGS. 8 and 9, a third embodiment of the invention is shown. Similar features are marked with the same reference numerals as the first and second embodiments, with an increase of 200 compared to the first embodiment.

In this third embodiment, the central absorbent material 208 is enveloped between a first permeable top sheet 207 and a first impermeable back sheet 240, said sheets 207, 240 being sealed together around their peripheries. Attached to the central portion of the backsheet 240 is a pleated arrangement similar to the previous embodiment of FIG. 1, in which however a second permeable top sheet 241 is attached to a second impermeable back sheet 242 at the outer edges thereof 215, 216 and also at least at each of the apices 219, 220 and inner edges 213, 214, and preferably therebetween. Sheet 241 is fixedly joined to sheet 242 at a central region 225, running longitudinally along the product. Also, elastic threads 232 and 233 have been provided in the same way as in FIG. 3 for example. It will however be noted that the outer edges 215, 216 of the lateral portions lie within the outer edges 243, 244 of the product 201. Thus, it is preferable if the central region of the elastic elements, when the pleats are unfolded, lie laterally outwardly of the central portions 245, 246 of edges 243, 244 at least over a major part of their unstretched length.

In this third embodiment, there are thus two structures which have been made separately and then attached together. This allows easy adaptation of standard flat products into products which can be transformed into basin-shaped products, by simply adding the self-contained pleated arrangement (i.e. the arrangement including, and comprised between, sheets 241 and 242) to the back sheet of any flat product. This also highlights the independent nature of the lateral movement capability of the lateral portions compared to any central absorbent portion 202.

As is apparent, in this embodiment, the portions 226 and 227 need not be in a position, when the surplus material of the pleat is unfurled, in which they will absorb bodily fluids, but instead their sole purpose only needs to be to help create a basin shape in the larger absorbent product part 208. Therefore, portions 226 and 227 do not need to have any absorbent material therein, but can be made of any suitable stiffening material. The stiffening material can also be omitted. Similarly, the portions 226, 227 preferably do not have an hour glass shape, but are simple flat rectangular strips 227, 228 as shown. However, the pleated portions and even the portions 226 and 227 can be arranged to have absorbent sections which project beyond the side edges 243, 244 in the folded-out or flat condition of the product.

There is no requirement that the seals 234 and 235 should include either of layers 207 or 240. Thus only the pleats second sheets 241, 242 need be sealed at the ends. However, for reasons of product integrity and appearance, it is preferable to seal all four sheets together across the pleats in the end regions of the product.

As a further alternative embodiment to the first and third embodiments shown and/or described above, it is also imaginable that each side of the double pleated part of the product lying on opposite sides of the longitudinal centreline could be formed by separate pieces of material. These pieces are materially separate from one another and each of said single pleat strips could be attached separately to a central absorbent core on either side of the longitudinal centre line. Each pleat should of course be sealed at its respective ends.

Figure 11:
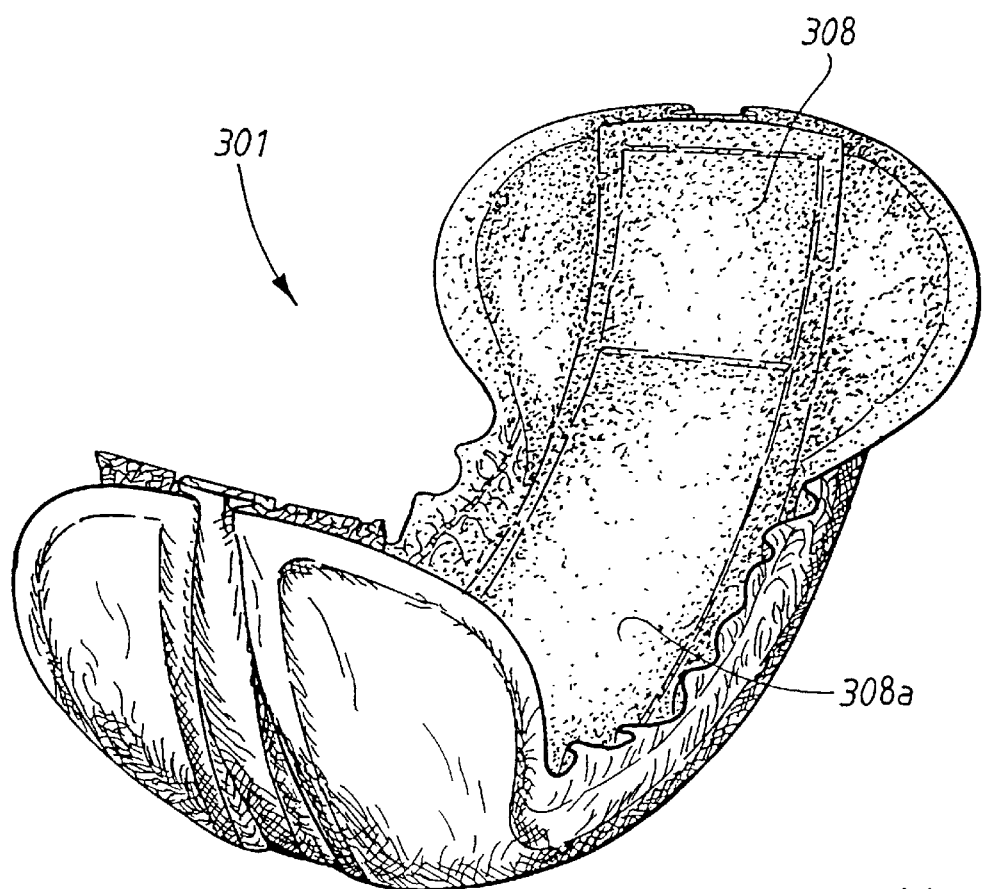
FIG. 11 shows a perspective view of a product similar to that in FIGS. 1 to 3 in the state where the double bottom pleat has been opened out along the majority of its length and in which an extra layer of superabsorbent material has been added to the central absorbent portion.
Figure 12:
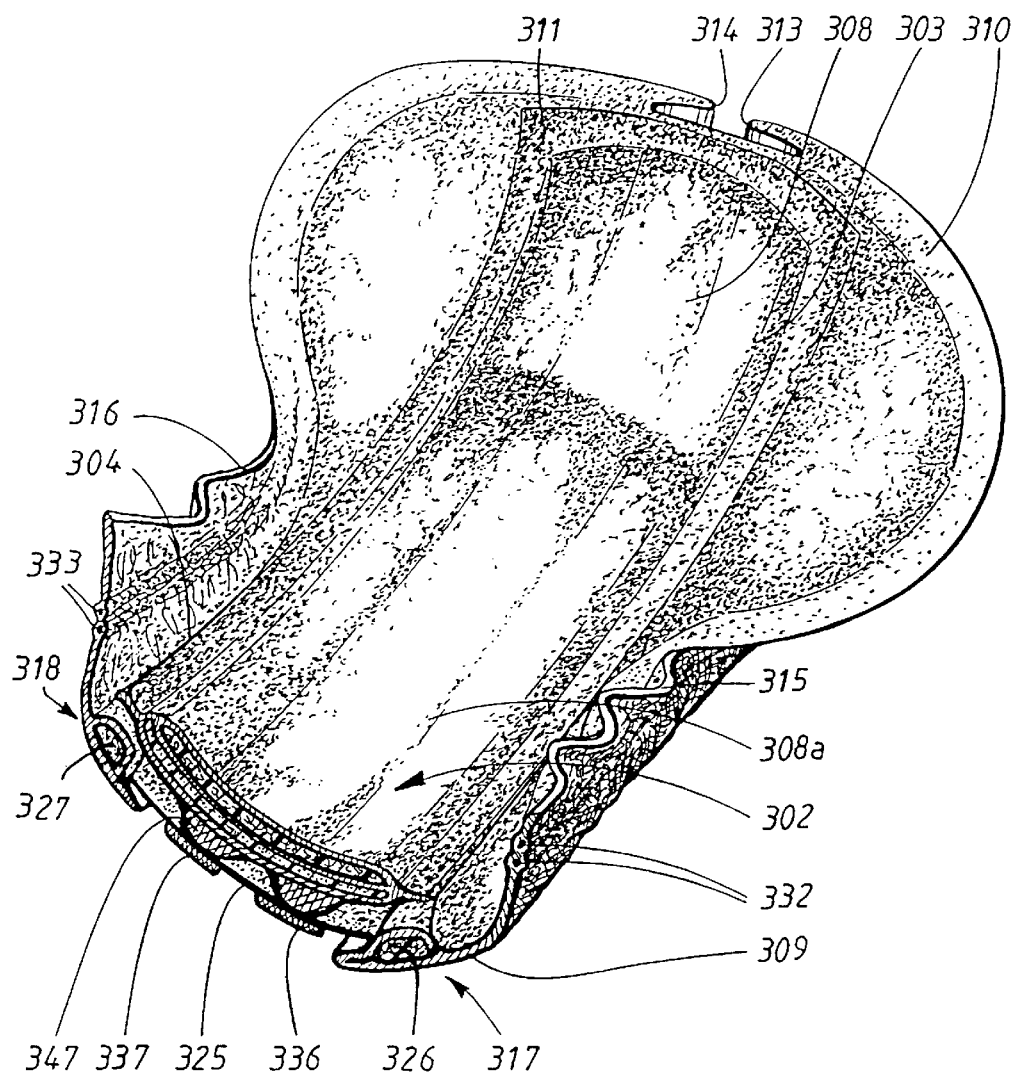
FIG. 12 shows a perspective, expanded view of the product in FIG. 11 cut laterally proximate its longitudinal centre.

In FIGS. 11 and 12, similar features are marked with the same reference numerals as the previous embodiments, with an increase of 300 compared to the first embodiment.

FIG. 11 is a schematic and perspective view of a product 301 according to the invention, very similar to that shown in FIGS. 4 to 7 and helps the reader to visualise the product. In this embodiment, the central absorbent core comprises two superposed absorbent portions, a larger absorbent portion 308 and a smaller centrally located portion 308*a*. Due to the central location of portion 308*a*, it is typically provided with a large amount of superabsorbent material or with fast-wicking material.

From FIG. 11, the basin shape of the product formed by the curvature in both lateral and longitudinal directions can be clearly seen.

FIG. 12 is a slightly enlarged view of the product in FIG. 11, which has been cut laterally at its longitudinal centreline. The relative dimensions of the various absorbent components 308, 308*a*, 326 and 327 and the various sheets may however vary from those shown. Adhesive connection strips 347 are shown in this embodiment, said strips 347 joining the back sheet and top sheet layers 309, 310 (in a combined region 325) to the lower side of central absorbent part 302.

The arrangement of the various embodiments of the invention can also be used as a part of a removable absorbent inlay or insert which is to be fitted to outer support structures for same. Such absorbent inserts or inlays are known per se, but these can be improved by using one or more aspects of the present invention.

Figure 13:
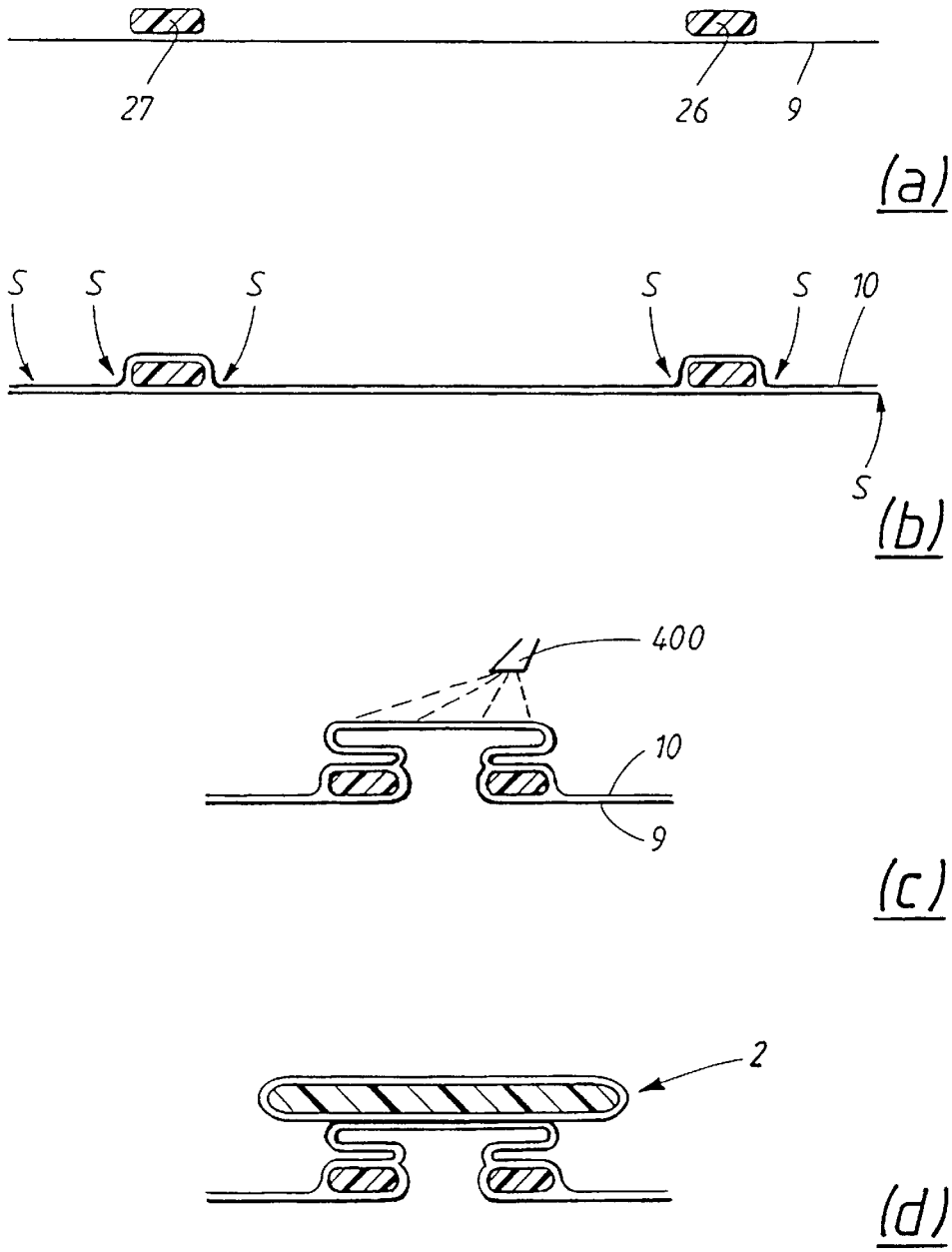
FIG. 13 shows four steps, denoted as steps (a) to (d), in the manufacturing process of the product in FIGS. 1 and 2.

One possible manufacturing method for the product of the first embodiment will now be described with reference to manufacturing steps (a) to (d) shown in FIG. 13.

In step (a), a back sheet 9 is fed on to a conveyor (not shown) and two stiffening, and preferably absorbent, members 26, 27 are attached to the backing sheet (e.g. by adhesive). Alternatively, pre-prepared sheets 9 with members 26 and 27 laminated thereon may be used.

In step (b) a permeable top sheet 10 is fed over the sheet 9 and the two members 26 and 27 and is sealed to sheet 9, at least at the locations indicated by arrows marked "S". Preferably the sheets are also sealed together between the indicated sealing locations "S". It should be remembered that the drawing is not to scale and thus that the sheets 9 and 10 would normally be the same width (i.e. from left to right on the drawing as depicted). Any slight difference in the distance spanned by the sheets 9 and 10 respectively (which might be required to enclose the members 26 and 27) would be accounted for by the inherent flexibility and/or possibly stretchability, and/or elasticity, of the sheets.

In step (c), a folding apparatus (not shown) is used to pleat the joined top and back sheets 9, 10 as shown, and a suitable means such as depicted means 400 may add adhesive, for example in the form of a spray, to the top of the pleat. Although shown as a very elevated structure, the product in step (c) in reality will be very thin.

The ends of the pleats on either side of the centreline may be sealed at this time by simple heat sealing jaws for example, applied at either longitudinal end of the product.

In step (d) the central absorbent portion 2 is added to the adhesive on the upper side of the sheet 10 and the product is basically complete and ready for stacking and packaging.

To manufacture products where there are only two sheets involved, such as in the second embodiment, the manufacturing process involves fixing the absorbent elements appropriately between the two sheets and then attaching them. Then the resulting intermediate product is merely pleated.

In FIG. 14, a typical method of manufacturing the article depicted in FIG. 7a is shown.

In step (a) the process is started with a top sheet 410, although a back sheet could be used. Thus, a top sheet 410 is fed on to a conveyor (not shown) and two stiffening, and preferably absorbent, members 426, 427 are attached to the top sheet (e.g. by adhesive). Alternatively, pre-prepared sheets 410 with members 426 and 427 laminated thereon may be used. Additionally, a third member 408 of absorbent material is added to the sheet 410. The members 426 and 427 will preferably be approximately equidistant from the outer edges of the absorbent 408 at any particular location along the length of the sheet 410 (i.e. in the plane perpendicular to the plane of the paper), although the actual distance between the laterally inner edge of element 426, 427 and the respective laterally outer edge of element 408 may vary along said length.

In step (b), a back sheet 409 is fed over the sheet 410 and the three members 408, 426 and 427. Sheet 409 is then sealed to sheet 410, at least at the locations indicated by the arrows marked "S". Although locations "S" are only shown on one side of the intermediate product, it should be understood that locations "S" are intended to be located on the opposite side also at locations symmetrical about the product centreline (as in FIG. 13). Preferably the sheets are also sealed together between the indicated sealing locations "S". Any slight difference in the distance spanned by the sheets 410 or 409 respectively, would be accounted for by the inherent flexibility and/or possibly stretchability, and/or elasticity, of the sheets.

Two strips of adhesive 440, 441 are placed on the upper surface of back sheet 409. The skilled man would however understand that this adhesive could also be applied earlier or later in the process of manufacture.

Similarly, strips 436, 437 of contact adhesive (which will ultimately be in contact with the user's clothing when worn in a folded-out state like that shown in FIG. 7).

A pleating apparatus (not shown) will then pleat the structure into its final shape, whereby the adhesive 440, 441 will be caused (by activation or contact, or in another way) to join sheet 409 to itself in the two inner folds of the pleat structure closest to the absorbent core 408, such that these joined areas of the sheet 409 are rendered "inactive" when the pleat structure is opened out. As will be clear to a skilled person, the position of the adhesive 440, 441 can vary to a large degree whilst still maintaining the required structure for operation of the pleat.

The method of FIG. 14 lends itself easily to high speed manufacture, especially due to the use of simple folding equipment for making the pleats.

Although the invention has been described above with reference to several preferred embodiments thereof, the scope of the invention is not limited thereto but is instead defined by the full scope of the appended claims.

For instance, although the double pleated embodiments have been shown as an approximately symmetrical arrangement, one of the two pleat portions may be shorter than the other.

It may also be remarked that where no specific treatment of the backsheet is foreseen to provide a release means, the release means could be provided by the material of the backsheet itself, although a careful balance of forces for opening the pleat(s) and not tearing during this process is required.

It is also possible to add further sheets or absorbent elements on either side of the sheets and absorbent/stiffening portions of the aforegoing embodiments, without departing from the underlying concepts of the present invention.

What is claimed is:

1. Absorbent product for absorbing bodily exudates, wherein said absorbent product has a longitudinal axis and a lateral axis and wherein said absorbent product comprises a central absorbent portion including an upper body-facing surface and a lower surface, said absorbent product further comprising at least a fluid-impermeable back sheet, wherein said absorbent product comprises two lateral portions, each including an inner edge and an outer edge extending in the longitudinal direction of said product, each of said inner edges being attached to said central absorbent portion by means of a surplus of material of said back sheet comprising at least part of at least one longitudinally arranged pleat in the back sheet material, wherein each of said inner and outer edges of said lateral portions can move in a lateral direction independently of said central absorbent portion.

2. Absorbent product according to claim 1, wherein stiffening means are provided at the inner edge of each lateral portion so as to provide a stiffened inner edge at least along a major portion of the longitudinal extent thereof.

3. Absorbent product according to claim 1, wherein each of said lateral portions comprises a fluid-permeable body-facing surface on one side and a fluid-impermeable layer on the opposite side, and in that absorbent material is positioned between said body facing surface and said fluid-impermeable layer, to thereby provide an absorbent product with three distinct and separate absorbent portions.

4. Absorbent product according to claim 3, wherein said fluid-impermeable layer of said lateral portions is constituted by said fluid-impermeable back sheet of said absorbent product.

5. Absorbent product according to claim 1, wherein a non-attached folded edge of said pleat forms the inner edge of each of said lateral portions.

6. Absorbent product according to claim 5 wherein said at least one pleat is sealed against opening at its ends.

7. Absorbent product according to claim 1, wherein friction-increasing means are provided on said fluid-impermeable back sheet, said friction-increasing means being arranged to increase frictional contact between said backsheet and a wearer's undergarment.

8. Absorbent product according to claim 7 wherein said friction-increasing means is a pressure-sensitive adhesive.

9. Absorbent product according to claim 7 wherein said friction-increasing means are provided on said fluid-impermeable back sheet at a location on said back sheet beneath said central absorbent portion, so as to allow said central absorbent portion to be positionally fixed with respect to a user's undergarment whilst allowing said lateral portions to move at least laterally with respect to said central absorbent portion.

10. Absorbent product according to claim 7, wherein the at least one pleat is arranged with respect to said backsheet so as to at least partially cover said friction-increasing means in the non-opened state of said pleat.

11. Absorbent product for absorbing bodily exudates, wherein said absorbent product has a longitudinal axis and a lateral axis, said absorbent product comprising:
a central absorbent portion including an upper body-facing surface and a lower surface,
at least a fluid-impermeable back sheet, and
two lateral portions, each including an inner edge and an outer edge extending in the longitudinal direction of said product, each of said inner edges being attached to said central absorbent portion by means of a surplus of material of said back sheet,
each of said inner and outer edges can move in a lateral direction independently of said central absorbent portion,
wherein friction-increasing means are provided on said fluid-impermeable back sheet, said friction-increasing means being arranged to increase frictional contact between said back sheet and a wearer's undergarment,
wherein at least one pleat is arranged with respect to said back sheet so as to entirely cover said friction-increasing means in the non-opened state of said pleat.

12. Absorbent product according to claim 3, wherein the absorbent material comprised in said lateral portions is thinner than the absorbent material of said central portion.

13. Absorbent product according to claim 12, wherein the thickness of the absorbent material of said lateral portions is less than 50% of the thickness of said central absorbent portion.

14. Absorbent product according to claim 13, wherein the thickness of the absorbent material of said lateral portions is in the range of 5% to 20% of the thickness of said central absorbent portion.

15. Absorbent product according to claim 3, wherein the absorbent material comprised in each of said lateral portions has a half hour-glass shape, with the curved outer edge of each of said half hour-glass shapes lying laterally outwardly and the straight inner edge thereof lying inwardly, such that the straight edges of each of said lateral portions lie opposite one another.

16. Absorbent product for absorbing bodily exudates,
wherein said absorbent product has a longitudinal axis and a lateral axis and
wherein said absorbent product comprises a central absorbent portion including an upper body-facing surface and a lower surface,
said absorbent product further comprising at least a fluid-impermeable back sheet,
wherein said absorbent product comprises two lateral portions, each including an inner edge and an outer edge extending in the longitudinal direction of said product, each of said inner edges being attached to said central absorbent portion by means of a surplus of material of said back sheet,
wherein each of said inner and outer edges of said lateral portions can move in a lateral direction independently of said central absorbent portion,
wherein each of said lateral portions is provided with elastication means allowing extension thereof in the longitudinal direction, said elastication means being located proximate the longitudinally-central part of the outer edge of each lateral portion.

17. Absorbent product according to claim 7, wherein said friction-increasing means is separated from contact with other surfaces of said backsheet by release means on a surface of said backsheet lying in contact with said friction-increasing means.

18. Absorbent product for absorbing bodily exudates, wherein said absorbent product has a longitudinal axis and a lateral axis and
wherein said absorbent product comprises a central absorbent portion including an upper body-facing surface and a lower surface,
said absorbent product further comprising at least a fluid-impermeable back sheet,
wherein said absorbent product comprises two lateral portions, each including an inner edge and an outer edge extending in the longitudinal direction of said product, each of said inner edges being attached to said central absorbent portion by means of a surplus of material of said back sheet,
wherein each of said inner and outer edges of said lateral portions can move in a lateral direction independently of said central absorbent portion,
wherein each of said lateral portions comprises a fluid-permeable body-facing surface on one side and a fluid-impermeable layer on the opposite side, and in that absorbent material is positioned between said body facing surface and said fluid-impermeable layer, to thereby provide an absorbent product with three distinct and separate absorbent portions,
wherein said fluid-impermeable layer of said lateral portions is constituted by said fluid-impermeable back sheet of said absorbent product, and
wherein a plurality of pleats are arranged in said back sheet.

19. Absorbent product according to claim 1, wherein said at least one pleat is a double pleat.

20. Absorbent product according to claim 1, wherein said central absorbent portion contains absorbent material which is surrounded on all sides by a fluid-permeable material.

21. Absorbent product according to claim 1 in which each of said lateral portions is provided with absorbent material positioned between a fluid-permeable layer and a fluid-impermeable layer, thereby forming lateral absorbent portions, wherein said product comprises only one fluid-impermeable back sheet layer and only one fluid-permeable top sheet layer, and wherein each of said absorbent portions is positioned between said top sheet layer and said back sheet layer.

22. Absorbent product according to claim 21, wherein the surplus material provided for connecting each of said lateral portions to said central portion has a length in the lateral direction such that when said surplus material is unfurled, the longitudinal inner edges of the lateral absorbent portions lie laterally inside the outer longitudinal edges of said central absorbent portion.

23. Absorbent product according to claim 21, wherein the surplus material provided for connecting said lateral portions to said central portion has a length in the lateral direction of said product such that when said surplus material is unfurled, the longitudinal inner edges of the lateral absorbent portions lie laterally adjacent to the outer longitudinal edges of said central absorbent portion, at least along a part of the length of said central portion.

24. Absorbent product for absorbing bodily exudates, wherein said absorbent product has a longitudinal axis and a lateral axis and wherein said absorbent product comprises a central absorbent portion including an upper body-facing surface and a lower surface, said absorbent product further comprising at least a fluid-impermeable back sheet, wherein said absorbent product comprises two lateral portions, each including an inner edge and an outer edge extending in the longitudinal direction of said product, each of said inner edges being attached to said central absorbent portion by means of a surplus of material of said back sheet, wherein each of said inner and outer edges of said lateral portions can move in a lateral direction independently of said central absorbent portion, and wherein said central absorbent portion is contained between an envelope comprising a first fluid-permeable top sheet and a first fluid-impermeable back sheet, and wherein said lateral portions are provided between a second fluid-permeable top sheet and a second fluid-impermeable back sheet, said first back sheet being connected to said second top sheet.

25. Absorbent product for absorbing bodily exudates, wherein said absorbent product has a longitudinal axis and a lateral axis and wherein said absorbent product comprises a central absorbent portion including an upper body-facing surface and a lower surface, said absorbent product further comprising at least a fluid-impermeable back sheet, wherein said absorbent product comprises two lateral portions, each including an inner edge and an outer edge extending in the longitudinal direction of said product, each of said inner edges being attached to said central absorbent portion by means of a surplus of material of said back sheet, wherein each of said inner and outer edges of said lateral portions can move in a lateral direction independently of said central absorbent portion, and wherein said central absorbent portion is attached to said surplus of material at attachment locations which are laterally inside the outer longitudinal edges of said central absorbent portion, to thereby allow the longitudinal edges of the central absorbent portion and also the part of the lower surface of the central absorbent portion which extends laterally inwardly from each of said outer longitudinal edges up to said attachment locations, to present a surface for direct absorption of fluids.

26. Absorbent product according to claim 1, wherein in a flattened state of said absorbent product, said two lateral portions at least partially underlie the lower surface of said central portion.

27. The absorbent product according to claim 1, wherein the absorbent product is an incontinence pad, sanitary pad, diaper, other absorbent garment, or an absorbent inlay.

28. The absorbent product according to claim 17, wherein the release means comprises silicon.

29. The absorbent product according to claim 20, wherein the fluid-permeable material surrounding the absorbent material of the central absorbent portion is non-woven.

* * * * *